United States Patent
Lafferty et al.

[11] Patent Number: 5,190,028
[45] Date of Patent: Mar. 2, 1993

[54] METHOD FOR MANUFACTURING A DISPOSABLE ARTHROSCOPIC PROBE

[75] Inventors: W. Michael Lafferty, Leucadia; George H. Middle, Canyon Lake, both of Calif.; Algis R. Banys, Reno, Nev.; Daniel S. Kline, Carlsbad, Calif.

[73] Assignee: Citation Medical Corporation, Reno, Nev.

[21] Appl. No.: 845,070

[22] Filed: Mar. 3, 1992

Related U.S. Application Data

[63] Continuation-in-part of Ser. No. 650,066, Feb. 4, 1991.

[51] Int. Cl.$^5$ ............................................. A61B 1/06
[52] U.S. Cl. ........................................ 128/6; 385/117
[58] Field of Search .......................... 128/4, 5, 6, 7, 8; 29/419.1; 385/117, 119

[56] References Cited

U.S. PATENT DOCUMENTS

| | | | |
|---|---|---|---|
| 3,297,022 | 1/1967 | Wallace | 385/117 |
| 3,581,376 | 6/1971 | Pilling | 29/419.1 |
| 4,251,448 | 3/1981 | Terada | 128/4 |
| 4,403,273 | 9/1983 | Nishioka | 385/117 |
| 4,589,404 | 5/1986 | Barath et al. | 128/6 |
| 4,590,923 | 5/1986 | Watanabe | 128/6 |
| 4,607,622 | 8/1986 | Fritch et al. | 128/6 |
| 4,615,333 | 10/1986 | Taguchi | 385/117 |
| 4,620,769 | 11/1986 | Tsuno | 350/96.26 |
| 4,736,733 | 4/1988 | Adair | 128/6 |
| 4,754,328 | 6/1988 | Barath et al. | 358/98 |
| 4,755,873 | 7/1988 | Kobayashi | 358/98 |
| 4,762,139 | 8/1988 | Hussein | 128/6 |
| 4,782,819 | 11/1988 | Adair | 128/6 |
| 4,844,071 | 7/1989 | Chen et al. | 128/6 |
| 4,867,138 | 9/1989 | Kubota et al. | 128/6 |
| 4,920,961 | 5/1990 | Grossi et al. | 606/14 |
| 4,947,245 | 8/1990 | Ogawa et al. | 358/98 |
| 5,005,943 | 4/1991 | Fort | 350/96.26 |

Primary Examiner—Cary E. O'Connor
Attorney, Agent, or Firm—Nydegger & Associates

[57] ABSTRACT

A method is provided for assembling an arthroscopic probe which includes bending a linear image-transmitting optical fiber about a heated pivot point so that the distal end of the fiber is oblique to the proximal end. A lens is then attached to the distal face of the image-transmitting optical fiber by means of an adhesive and the resulting image path is positioned in a hollow needle with the lens exposed at the distal end and the optical fiber exposed at the proximal end. An illuminating optical fiber is also positioned in the needle adjacent the image path and the two are anchored therein by a curable filler material. Finally, the needle is proximally mounted in a base such that the proximal faces of the image-transmitting and illuminating optical fibers are exposed.

24 Claims, 2 Drawing Sheets

METHOD FOR MANUFACTURING A DISPOSABLE ARTHROSCOPIC PROBE

This is a continuation-in-part patent application of copending U.S. patent application Ser. No. 07/650,066 filed on Feb. 4, 1991 and entitled "Portable Arthroscope With Periscope Optics" pending.

FIELD OF THE INVENTION

The present invention relates generally to the manufacture of medical diagnostic devices, and particularly to the manufacture of arthroscopes. The present invention more particularly, though not exclusively, relates to the manufacture of disposable arthroscopic probes having a relatively large internal viewing field within a living body.

BACKGROUND OF THE INVENTION

In the field of medicine, modern techniques have been developed for diagnosing damage to the interior structure of a living body. One such technique is arthroscopy, which is most commonly used to examine the interior structure of bone joints, such as the knee joint, and to determine the existence and extent of any damage in the joint. A significant advantage of arthroscopy is that it permits internal viewing of the body joint without requiring conventional invasive surgery to externally expose the joint. Furthermore if joint damage is discovered during the examination, relatively non-invasive corrective surgery can be performed in conjunction with the arthroscopic examination to repair the joint damage.

Arthroscopic examination employs a device termed an arthroscope having a probe and an imaging device that cooperate with a video display. In operation, the probe is inserted into the joint being examined while it is connected to the imaging device which in turn communicates with the video display, thereby generating a picture of the interior structure of the joint. Consequently, the operator of the arthroscope is able to view, real-time, the interior structure of the joint while the probe is in place in the joint. This enables rapid diagnosis of any damage to the joint and the prescription of appropriate treatment.

Due to strict performance requirements, particularly with respect to image quality and field of viewing, arthroscopes require a high degree of precision and, thus, are extremely costly to manufacture. It is, therefore, a virtual economic necessity that arthroscopes accommodate reuse. Accordingly, reusable arthroscopes, and particularly the probe, must be sterilized before each use to prevent infection of the patient with a contaminated needle. Nevertheless, the possibility exists for improper sterilization of the needle assemblies, or even for recontamination of the needle assemblies during handling following sterilization, either of which could infect the patient.

An optimal solution to the problem of patient infection would be to employ prepackaged sterile non-reusable arthroscopes in all arthroscopic procedures. Unfortunately no known method exists for manufacturing an arthroscope, which can be cost-effectively disposed after a single use, yet which meets the strict performance requirements for arthroscopic procedures.

As such, it is an object of the present invention to provide a cost-effective method for manufacturing interchangeable arthroscopic needle assemblies that are disposable after each use. It is further an object of the present invention to provide a method for manufacturing disposable arthroscopic needle assemblies that meet or exceed the performance requirements for known arthroscopic procedures.

SUMMARY

The present invention is a method for manufacturing a relatively inexpensive disposable arthroscopic probe. The method generally encompasses attaching a lens onto the end of an image guide, thereby forming a continuous image path, and threading the image path through a hollow needle along with an optical fiber bundle that serves as an illumination path. The needle containing the image and illumination paths is mounted onto a base to produce the finished arthroscopic probe.

Preliminary to attachment of the lens onto the image guide, a number of preparatory steps are performed. In particular, a distal bend having a predetermined angle of curvature is placed in the linear image guide by thermal deformation. The tip of the distal end is then cut to a predetermined length and ground flat so that it will fit flush with the proximal face of the lens during subsequent attachment thereto. As an additional preparatory step the distal face of the image guide is polished to enhance its light transmitting ability.

The lens is attached to the bent image guide by aligning the two in an end to end manner. With the faces so aligned, a continuous coating of an adhesive is applied to the proximal face of the lens and/or the distal face of the image guide. The faces are then joined together in close continuous contact and the adhesive is cured to effect a strong permanent bond between the lens and guide, thereby completing assembly of the image path.

The image path is positioned in the needle by feeding the path through the interior passageway of the needle such that the lens is positioned slightly interior to the distal end of the needle while a portion of the image guide extends from the proximal end of the needle. The fiber optic bundle which serves as the illumination path is additionally threaded through the passageway to extend side-by-side with the image path through the needle and out the proximal end thereof. A filler is placed in the interstitial space at the distal end of the passageway which is preferably a curable resin. Upon curing, the resin anchors the image and illumination paths in the needle. An opaque resin may be selected as the filler which serves to reduce light clutter between the image and illumination paths.

Manufacture of the arthroscopic probe is completed by mounting the needle onto the base and finishing the image and illumination paths at both the distal and proximal ends of the arthroscopic probe. The base is a hollow body having a needle inlet orifice centrally formed at its distal end and two outlet orifices formed at its proximal end. One outlet orifice is centrally aligned to receive the proximal end of the image path and the other outlet orifice receives the proximal end of the illumination path.

Mounting is accomplished by sliding the proximal end of the needle, having the image and illumination paths extending therefrom, into the needle inlet orifice of the base. A rubber gasket may be fitted between the needle and the inlet orifices to provide a close fit and to compensate for possible variations in thermal expansion between the materials of the needle and the base. The proximal end of the needle is positioned within the interior of the base such that the proximal end of the image path extending from the needle aligns with its outlet orifice for insertion therein. Meanwhile the portion of the illumination path extending from the needle, which is generally more flexible than the image path, is radially displaced from the proximal end of the needle for alignment and insertion into the remaining outlet orifice.

With the needle so mounted in the base, a filler, such as that employed in the needle, is injected into the hollow interior of the base. The filler occupies the interior of the base as well as any interstitial spaces in the orifices of the base after their respective members have been inserted therein. The filler is cured to anchor the proximal ends of the needle, image path and illumination path in the base.

The distal end of the probe is finished by cutting or grinding the distal end from opposite sides thereof at oblique angles relative to the longitudinal axis of the needle, thereby forming a convex v-shaped tip at the distal end of the needle. By removing portions of the distal end of the needle, the lens and optical fiber bundle contained therein are exposed to the external environment. Furthermore, although the distal end of the needle is obliquely oriented relative to the longitudinal axis of the needle, it is nevertheless parallel to the distal face of the lens due to the curvature of the image path. Accordingly, the enhanced ability of the lens to receive external light is not diminished by cutting and grinding.

The proximal end of the probe is finished by cutting off the portions of the image or illumination paths extending proximally from the outlet orifices of the base. The paths are cut flush with the proximal surface of the base and are polished at their exposed ends to similarly optimize their light transmitting ability. The product resulting from the above-described manufacturing method is a relatively inexpensive disposable arthroscopic probe that is made to strict tolerances, and accordingly is capable of superior performance when incorporated into an arthroscope for diagnostic or other medical procedures.

The present invention will be further understood from the accompanying drawings in conjunction with the accompanying description, in which similar reference characters refer to similar parts.

DESCRIPTION OF PREFERRED EMBODIMENT

The present invention is a method for manufacturing an arthroscopic probe. A representative probe which can be manufactured according to this method is initially described below, thereby establishing a context in which to describe the method of the invention.

Figure 1:
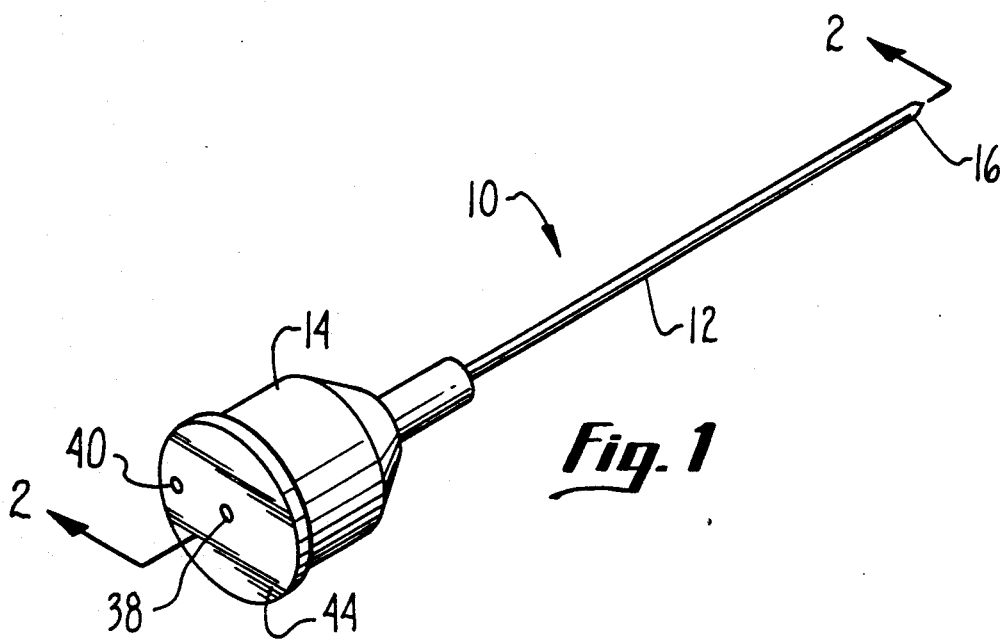
FIG. 1 is a perspective view of an arthroscopic probe produced according to the method of the present invention.

Referring first to FIG. 1, an arthroscopic probe is shown and generally designated 10. Arthroscopic probe 10 has a needle 12 mounted on a base 14. Needle 12 is a hollow cylindrical tube formed from a high-strength, biologically-compatible material such as stainless steel. Base 14 is preferably formed from a sturdy lightweight rigid plastic. Base 14 is at the proximal end of arthroscopic probe 10 and needle 12 is at the distal end thereof. The terms proximal and distal, as used herein, refer to the relative distance of the particular probe component from the probe operator when the probe is being used in an arthroscopy procedure.

Figure 2:
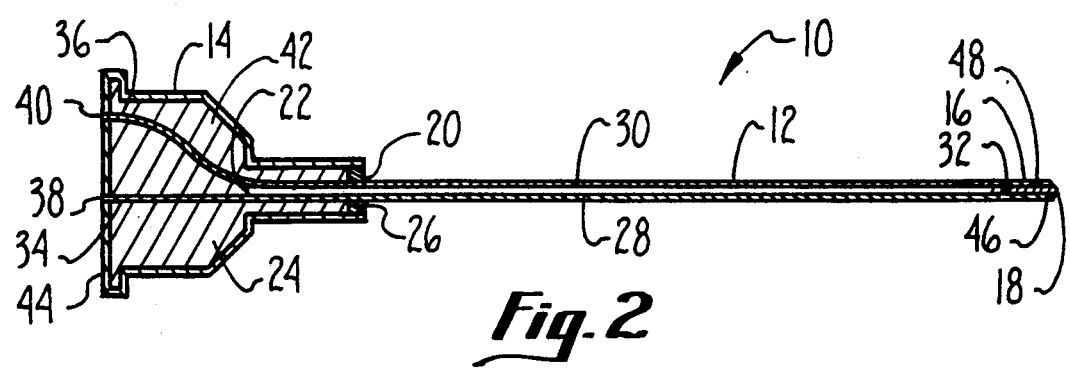
FIG. 2 is a cross-sectional view of the arthroscopic probe of the present invention as seen along line 2—2 in FIG. 1.

Cross-referencing to FIG. 2, needle 12 has a distal end 16 terminating in a sharpened tip 18. Base 14 has a distal orifice 20 to receive proximal end 22 of needle 12 into base interior 24. Distal orifice 20 may be provided with a rubber gasket 26 to secure needle 12 therein. Positioned within needle 12 is an image path 28 and an illumination path 30, anchored by a solid filler material 32 at distal end 16.

Image path 28 and illumination path 30 have proximal ends 34 and 36 respectively, which extend from proximal needle end 22 through base interior 24. Proximal ends 34 and 36 are received by proximal orifices 38 and 40 respectively of base 14 and terminate flush with the proximal end 44 of base 14. A solid filler material 42 occupies the bulk of base interior 24 as well as any portions of proximal orifices 38, 40 not occupied by proximal ends 34, 36 respectively.

Image path 28 and illumination path 30 have distal ends 46 and 48 respectively which are exposed at sharpened needle tip 18. Distal ends 46 and 48 are described in greater detail below with reference to FIGS. 3 and 4 and the method of the present invention. It is further noted that additional arthroscopic equipment not described herein is employed for operational support of arthroscopic probe 10 in the performance of arthroscopic procedures. A description of such equipment and its method of operation is disclosed in U.S. patent application Ser. No. 07/650,066, filed on Feb. 4, 1991, and entitled "Portable Arthroscope With Periscope Optics", and as such is incorporated herein by reference.

Figure 3:
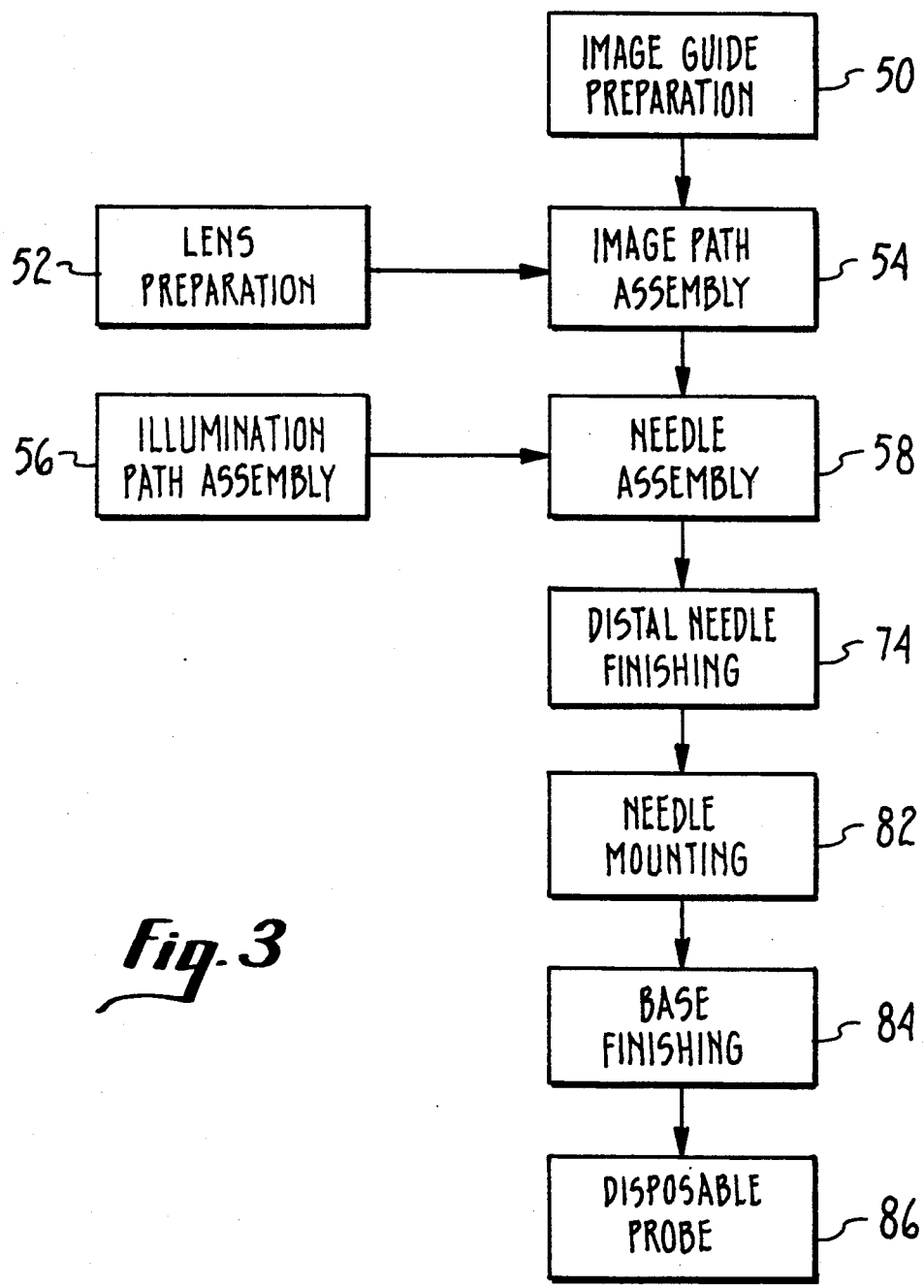
FIG. 3 is a flow chart of the method of manufacture of the present invention.

Referring to FIG. 3, a flow chart schematically depicts the method of the present invention for manufacturing an arthroscopic probe such as arthroscopic probe 10 shown in FIGS. 1 and 2. In initial step 50, an image guide is prepared for subsequent assembly of an image path. The image guide is an optical fiber that has the geometry of a straight elongated cylindrical solid with a proximal face and a distal face. Being an optical fiber, the image guide is composed of ultra-pure glass capable of conducting modulated light signals by total internal reflection. Although the image guide appears to be a single unitary construct, the optical fiber forming the image guide may in fact be a plurality of smaller fibers which are integrated into the single unitary construct.

Preparation of the image guide entails stripping any exterior opaque coating which may be present away from the distal end of the guide. Such a coating may be present on the sides of the optical fiber to prevent light from entering the fiber through its sides. The coating, however, is a hindrance to bending the image guide, as will be described below, thereby necessitating its removal. After stripping, the image guide is cut at its proximal end to a predetermined length and the resulting proximal face is polished for optical optimization.

The next sequence under step 50 is bending of the image guide at its distal end. Bending is accomplished by fixing the proximal end of the image guide in a clamp while the distal end is freely suspended. A heat source, such as a high temperature flame from a torch, is rapidly applied for a predetermined time to a point on the distal end a short distance behind the tip thereof to raise the point to a predetermined temperature sufficient to render the distal end pliant at that point. Although the present invention is not so limited, it has been found under some conditions that a flame, having a temperature of about 2760° C., applied to a point on the distal end of the image guide for about 700 milliseconds will raise that point to a temperature of about 1650° C. which is generally sufficient to perform the bending step. At this temperature, the tip pivots downward under its own weight about the point of pliancy to produce a bend in the distal end having a predetermined angle of curvature. This angle is in a range of about 10° to 45°, preferably in a range of about 20° to 30°, and most preferably about 25°. If needed, an external weight can additionally be applied to the distal tip to facilitate bending thereof.

Upon cooling, a predetermined length at the tip of the bent distal end is cut off. The distal face is then ground with a grinder to render its surface orthogonal with the longitudinal axis of the guide at the tip of the distal end. As a final sequence in step 50, the ground distal face is polished to optimize its light transmitting ability. It is to be noted that step 50 and subsequent steps thereafter are performed in a relatively dust-free environment to avoid contamination of the optical surfaces. Quality control testing may be performed on the optical surfaces at each step to insure optimal light transmitting characteristics.

An adjunct to image guide preparation step 50 is lens preparation step 52, wherein a lens is provided for subsequent attachment onto the distal face of the image guide. The lens of choice is a gradient refractive index (GRIN) lens which is relatively shorter compared to the image guide, but has a substantially similar cross-sectional profile and has flat proximal and distal faces. Lens preparation comprises cleaning and quality control testing thereof.

Having prepared the image guide and lens, they may be assembled according to step 54 to form the image path 28 as shown with cross-reference to FIG. 2. Step 54 comprises applying a continuous coating of high-strength curable adhesive to the distal face of the image guide and/or the proximal face of the lens. The two faces are then aligned and fitted flush against one another in close contact. Care is taken to maintain the faces in tight fitting contact during curing of the adhesive.

The particular manner in which the adhesive is cured is a function of the actual adhesive, as will be apparent to one skilled in the art. A preferred adhesive in the present method is one curable by ultra-violet radiation. Accordingly, curing is performed by placing the assembled image path 28 in communication with a UV source for a predetermined time period to effect a strong and permanent bond between the lens and guide. At this point a wax cap (not shown) may be placed over the distal face of the lens to protect it during further manufacturing steps, but for removal from the face upon completion of arthroscopic probe 10 in a manner described hereafter.

After curing of the adhesive, the image path 28 is in a condition for assembly into needle 12. Preliminary thereto, the illumination path 30 is assembled in step 56. Assembly of illumination path 30 comprises coaxially bunching a predetermined number of individual optical fibers and cutting them to a predetermined length. Image path 28 and illumination path 30 are then threaded through the proximal end 22 of needle 12 in needle assembly step 58. Assembly step 58 positions paths 28, 30 within needle 12 adjacent each other such that their respective proximal ends 34, 36 extend from proximal needle end 22 while their respective distal ends 46, 48 remain interior to distal needle end 16 as shown in FIG. 2.

Needle assembly step 58 further comprises placement of a filler 32 that is preferably a curable epoxy resin within distal end 16 of needle 12 adjacent image and illumination paths 28, 30. The filler 32 may be placed in distal end 16 by coating paths 28, 30 with filler 32 prior to threading them through needle 12 or by extruding the filler 32 into distal end 16 after placement of paths 28, 30 therein. If the filler is an epoxy resin, it is preferably cured in distal end 16 by placement of the assembled needle in an oven for a time period between about 0.5 to 4 hours at a temperature between about 40° and 60° C. It is further desirable that the filler 32 is substantially opaque upon curing to reduce light clutter between the image and illumination paths 28, 30.

Figure 4:
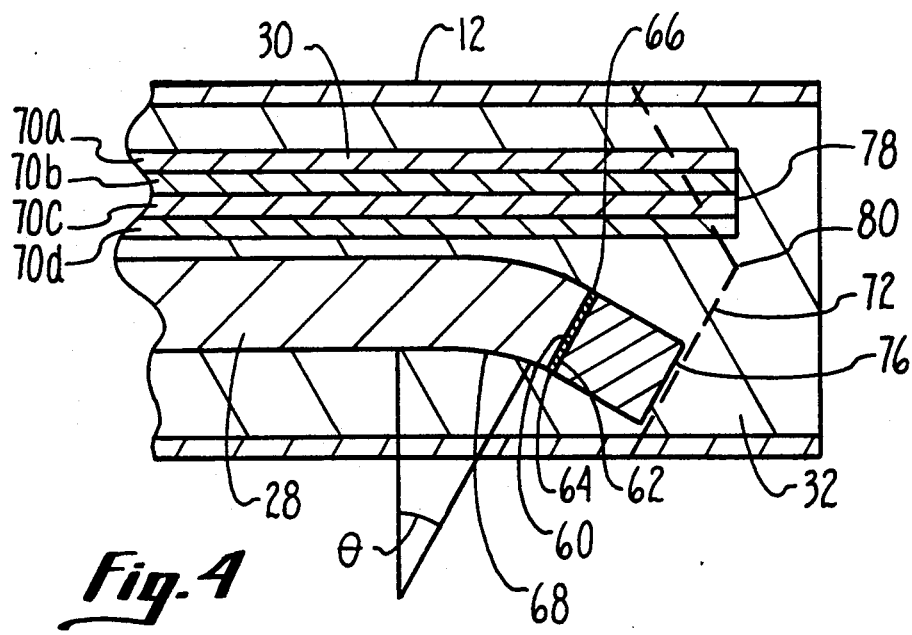
FIG. 4 is a schematic cross-sectional close-up view of the distal end of the arthroscopic probe of the present invention shown in FIG. 2.

FIG. 4 shows in close-up the distal end 16 of needle 12 at the completion of assembly step 58. As described above, image guide distal face 60 is aligned with lens proximal face 62 and adhered thereto by means of continuous adhesive coating 64 at the junction 66 between faces 60, 62 to form image path 28. The bend 68 is shown on image path 28 behind face 60 having an angle of curvature designated by $\theta$. Adjacent to image path 28 is illumination path 30 having a plurality of discrete optical fibers 70. Sufficient filler 32 occupies the remainder of the needle interior not occupied by paths 28, 30 to secure paths 28, 30 therein. A dashed line 72 across needle distal end 16 indicates the planes along which portions of distal end 16 are removed by cutting or grinding therethrough as described with reference to FIG. 3.

The next step of the present method shown in FIG. 3 is the distal needle finishing step 74 wherein the pointed tip 18 as shown in FIGS. 2 and 4 is completed. Step 74 basically comprises removing filler 32 and the frontal portions of the wax cap (if present) from the distal lens face 76, thereby exposing it to the external environment. This may be performed by grinding or cutting distal end 16 at an oblique angle relative to the longitudinal axis of needle 12. The cutting or grinding angle, although oblique relative to needle 12, is parallel to distal lens face 76 due to bend 68. Step 74 is continued by performing a second oblique cutting or grinding procedure through needle 12 originating at a point substantially opposite the first cutting or grinding procedure to expose the distal illumination path face 78 while forming point 80 on needle tip 18. The two oblique angles cuts are shown in FIG. 4 with reference to dashed line 72. Step 74 is completed by finely polishing face 78 for optimum light transmission.

Assembly of the disposable arthroscopic probe 10 is completed by performance of needle mounting step 82 and base finishing step 84. Step 82 comprises placement of the proximal needle end 22 into distal orifice 20 of base 14 having gasket 26 positioned therein to provide a seal. Concurrently, proximal image path end 34 which extends from proximal needle end 22 is inserted into proximal base orifice 38 while proximal illumination path end 36 is inserted into proximal base orifice 40. Mounting step 82 further comprises placement of a filler 42 in base interior 24. Filler 42 is preferably substantially identical to preferred filler 32 in needle 12. Filler 42 may be placed in interior 24 by injection through an injection orifice (not shown) in base 14 and is subsequently cured by placing the entire assembled arthroscopic probe 10 in an oven for a predetermined period of time at a predetermined temperature.

Base finishing step 84 comprises the cutting of any portions of image or illumination paths 28, 30 which may extend proximally from base orifices 38, 40. The cut is flush with the proximal base end 44 and the proximal faces of the paths 28, 30 are then polished to optimize their light transmitting ability. The resulting product shown by step 86 is a disposable arthroscopic probe 10.

While the particular method of manufacturing an arthroscopic probe as herein shown and disclosed in detail is capable of obtaining the objects and providing the advantages hereinbefore stated, it is to be understood that this method is merely illustrative of presently preferred embodiments of the invention and that other embodiments are possible within the scope of the present invention.

I claim:

1. A method for assembling an arthroscopic probe comprising:
   bending a substantially linear image-transmitting optical fiber having a proximal end and a distal end about a pivot point to render said distal end oblique relative to said proximal end;
   attaching a lens to said oblique distal end of said image-transmitting optical fiber to form an image path; and
   positioning said image path in a hollow needle having an open proximal end and an open distal end wherein said lens is at said open distal end and said image-transmitting optical fiber is at said open proximal end of said needle to form said arthroscopic probe.

2. A method for assembling an arthroscopic probe as recited in claim 1 wherein said bending step comprises:
   affixing said proximal end of said image-transmitting optical fiber to a stationary member while suspending said distal end of said image guide in free space;
   heating said pivot point to a predetermined deformation temperature, wherein said pivot point is pliable; and
   bending said distal end of said image-transmitting optical fiber downward under a force.

3. A method for assembling an arthroscopic probe as recited in claim 2 wherein said force is a gravitational force.

4. A method for assembling an arthroscopic probe as recited in claim 2 wherein said force is an externally applied force.

5. A method for assembling an arthroscopic probe as recited in claim wherein said lens is a gradient refractive index (GRIN) lens.

6. A method for assembling an arthroscopic probe as recited in claim 1 wherein said oblique distal end of said image-transmitting optical fiber has side walls and a distal face, and further wherein said distal face is orthogonal with said side walls.

7. A method for assembling an arthroscopic probe as recited in claim 6 wherein said lens has side walls, a proximal face and a distal face, and further wherein said proximal face and said distal face are orthogonal with said side walls.

8. A method for assembling an arthroscopic probe as recited in claim 7 wherein said lens is attached to said image-transmitting optical fiber by means of an adhesive applied between said proximal face of said lens and said distal face of said image-transmitting optical fiber.

9. A method for assembling an arthroscopic probe as recited in claim 1 wherein said distal end of said image-transmitting optical fiber is bent to an angle of curvature between about 20° and 30°.

10. A method for assembling an arthroscopic probe as recited in claim 1 wherein said proximal end of said image-transmitting optical fiber has a longitudinal axis substantially parallel to the longitudinal axis of said needle and said distal end of said image-transmitting optical fiber has a longitudinal axis oblique to the longitudinal axis of said needle.

11. A method for assembling an arthroscopic probe as recited in claim 1 further comprising mounting said open proximal end of said needle in a base.

12. A method for assembling an arthroscopic probe as recited in claim 11 wherein said needle is positioned in a distal orifice formed in said base such that said open proximal end of said needle extends into said base and said image-transmitting optical fiber is exposed to the exterior of said base via a proximal orifice formed in said base.

13. A method for assembling an arthroscopic probe as recited in claim 1 further comprising positioning an illuminating optical fiber in said needle adjacent said image path.

14. A method for assembling an arthroscopic probe as recited in claim 1 further comprising placing a filler material in said needle to anchor said image path therein.

15. A method for assembling an arthroscopic probe as recited in claim 14 wherein said filler material is a curable resin.

16. A method for assembling an arthroscopic probe as recited in claim 1 wherein said lens is exposed to the exterior of said needle via said distal open end.

17. A method for assembling an arthroscopic probe comprising:
   providing a substantially linear image-transmitting optical fiber having a proximal end with a proximal face and a distal end with a distal face;
   bending said image-transmitting optical fiber about a pivot point such that the longitudinal axis of said distal end is oblique to the longitudinal axis of said proximal end;
   providing a lens having a proximal face and a distal face;
   attaching said proximal face of said lens to said distal face of said image-transmitting optical fiber, thereby forming an image path, wherein the longitudinal axis of said lens is parallel with the longitudinal axis of said distal end of said image-transmitting optical fiber, and further wherein said proximal face of said lens and said distal face of said image-transmitting optical fiber are orthogonal to the longitudinal axes of said lens and said distal end of said image-transmitting optical fiber;
   positioning said image path in a hollow needle having an open proximal end and an open distal end, wherein said distal face of said lens is exposed to the exterior of said needle via said open distal and, and further wherein said proximal face of said image-transmitting optical fiber is exposed to the exterior of said needle via said open proximal end;
   positioning an illuminating optical fiber having a proximal face and a distal face in said hollow needle adjacent said image path, wherein said proximal face of said illuminating optical fiber is exposed to the exterior of said needle via said open distal end;

placing a curable filler material in said hollow needle;

curing said filler material to anchor said image path and said illuminating optical fiber in said needle; and mounting said proximal end of said needle in a base to form said arthroscopic probe, wherein said proximal faces of said image-transmitting and illuminating optical fibers are exposed to the exterior of said base.

18. A method for assembling an arthroscopic probe as recited in claim 17 wherein said needle is positioned in a distal orifice of said base, said proximal face of said image-transmitting optical fiber is positioned in a first proximal orifice of said base, and said proximal face of said illuminating optical fiber is positioned in a second proximal orifice of said base.

19. A method for assembling an arthroscopic probe as recited in claim 17 further comprising placing a curable filler material in said base and curing said filler material to anchor said proximal end of said needle in said base.

20. A method for assembling an arthroscopic probe comprising:

providing an image-transmitting optical fiber having a proximal end with a proximal face and a distal end with a distal face, wherein the longitudinal axis of said distal end is oblique to the longitudinal axis of said proximal end;

providing a lens having a proximal face and a distal face;

attaching said proximal face of said lens to said distal face of said image-transmitting optical fiber, thereby forming an image path, wherein the longitudinal axis of said lens is parallel with the longitudinal axis of said distal end of said image-transmitting optical fiber, and further wherein said proximal face of said lens and said distal face of said image-transmitting optical fiber are orthogonal to the longitudinal axes of said lens and said distal end of said image-transmitting optical fiber;

positioning said image path in a hollow needle having an open proximal end and an open distal end, wherein said distal face of said lens is exposed to the exterior of said needle via said open distal end, and further wherein said proximal face of said image-transmitting optical fiber is exposed to the exterior of said needle via said open proximal end; and mounting said proximal end of said needle in a base to form said arthroscopic probe, wherein said proximal face of said image-transmitting optical fiber is exposed to the exterior of said base.

21. A method for assembling an arthroscopic probe as recited in claim 20 further comprising positioning an illuminating optical fiber having a proximal face and a distal face in said hollow needle adjacent said image path, wherein said proximal face of said illuminating optical fiber is exposed to the exterior of said needle via said open distal end.

22. A method for assembling an arthroscopic probe as recited in claim 21 further comprising placing a curable filler material in said hollow needle and curing said filler material to anchor said image path and said illuminating optical fiber in said needle.

23. A method for assembling an arthroscopic probe as recited in claim 21 wherein said needle is positioned in a distal orifice of said base, said proximal face of said image-transmitting optical fiber is positioned in a first proximal orifice of said base, and said proximal face of said illuminating optical fiber is positioned in a second proximal orifice of said base.

24. A method for assembling an arthroscopic probe as recited in claim 20 further comprising placing a curable filler material in said base and curing said filler material to anchor said proximal end of said needle in said base.

* * * * *